United States Patent [19]

Saravis

[11] Patent Number: 4,593,843

[45] Date of Patent: Jun. 10, 1986

[54] SURGICAL STAPLER FOR IMPLANTING SUTURES

[76] Inventor: Lawrence M. Saravis, 23 Yale Ave., Milford, Conn. 06460

[21] Appl. No.: 410,936

[22] Filed: Aug. 24, 1982

[51] Int. Cl.$^4$ ............................................. A61B 17/04
[52] U.S. Cl. ...................................... 227/19; 74/109; 227/DIG. 1
[58] Field of Search ......................... 74/109, 110, 422; 227/19, DIG. 1, 83

[56] References Cited

U.S. PATENT DOCUMENTS

| | | | |
|---|---|---|---|
| 911,676 | 2/1909 | Pearson | 227/DIG. 1 |
| 1,760,652 | 5/1930 | Loomis | 74/110 X |
| 1,926,174 | 9/1933 | Reilly et al. | 74/110 X |
| 3,353,167 | 11/1967 | Daniels | 74/109 X |
| 3,777,355 | 12/1973 | Cooke | 227/DIG. 1 |
| 3,777,580 | 12/1973 | Brems | 74/110 |
| 4,169,476 | 10/1979 | Hiltebrandt | 227/DIG. 1 |
| 4,364,507 | 12/1982 | Savino | 227/DIG. 1 |

*Primary Examiner*—Paul A. Bell
*Attorney, Agent, or Firm*—Stephen E. Feldman

[57] ABSTRACT

A disposable surgical stapler having an overall hypodermic shape and a geared plunger mechanism, which gives a mechanical advantage. One of the improvements is the hypodermic configuration, which permits the surgeon to suture or staple without twisting his hand or the flesh of the patient. A magazine feed supplies the sutures or staples to the applying head at an advantageous angle. The major salient points of distinction of the present configuration are the geared plunger entailing the gearing (large and small gear), and parallel toothed racks, which gives a mechanical advantage; the upstop for the pusher and plunger, which serves to position the top of the pusher, so that in transit the staple cannot get twisted or suck back; the swivel top and hypodermic-like shape and arrangement, which permits the surgeon to suture or staple without twisting his hand, or the flesh or skin of the patient; improved visibility when implanting the staples, the staples are visible when coming out of the device, due to the vertical arrangement; and the advantageous feed angle of the staples, combined with other mechanism in the device, to give improved feeding of the staples via the magazine feed.

10 Claims, 5 Drawing Figures

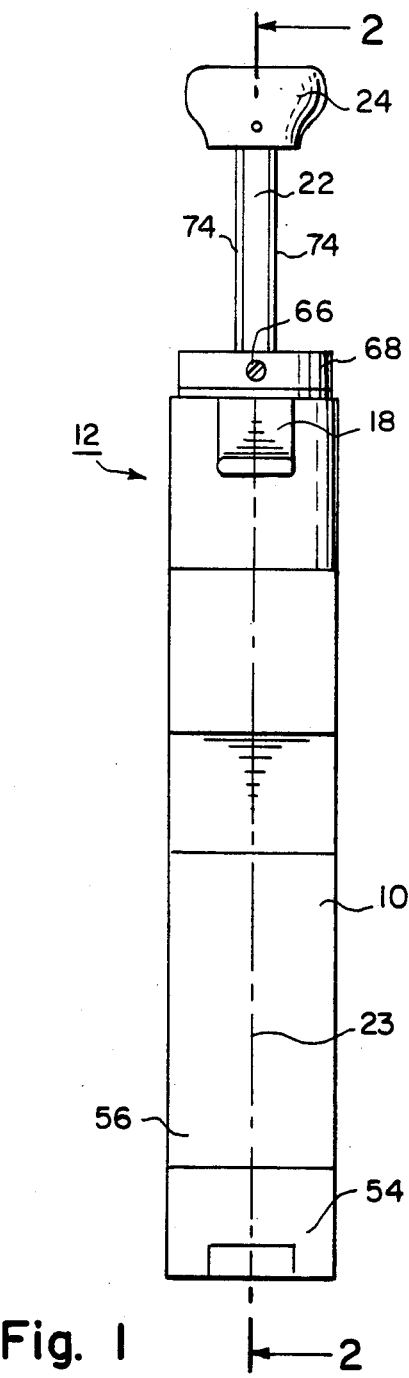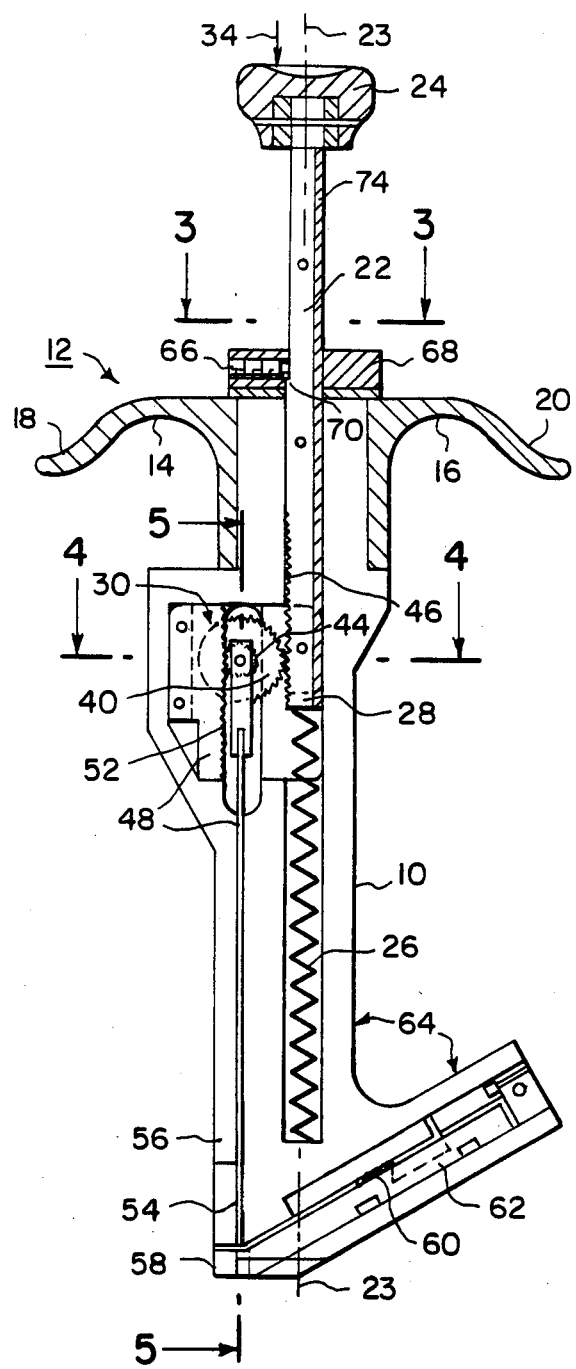
Fig. 1
Fig. 2

SURGICAL STAPLER FOR IMPLANTING SUTURES

BACKGROUND OF THE INVENTION

1. Field of the Invention

A surgical stapler for implanting sutures or staples in the fascia, skin or flesh of a human subject, so as to close an incision or wound, or to repair internal organs after an operation on the human subject.

2. Description of the Prior Art

Medical doctors and others in medical science and the healing arts often prescribe an operation as the indicated therapy to correct a medical problem in a human or animal subject, e.g., appendicitis or a tumor, a birth defect, etc., or to repair a wound or injury caused by e.g., a gunshot, an industrial or automobile accident, etc. Clinically speaking, the prognosis for most medical, surgical or dental operations is good, provided inter alia that the surgical incision or the wound, etc. is properly closed after the operation by bringing together the respective parts, such as flesh, fascia, or skin, so as to close the opening in the body and thereby promote healing.

In the early days of the development of the medical arts as a science, it was common practice to close an incision or wound in the body, or in a bodily organ, by suturing the parts together by sewing, using a needle and thread, such as catgut. Such a procedure was lengthy and time-consuming, did not produce tight or ample closure in some instances, and lent itself to contamination of the incision, organ or wound with germs or foreign agents, leading to infection.

A recent development in this field has been the surgical stapler, which has superceded the sewing technique in most cases of medical practice and surgery, whether in the doctor's or dentist's office, in hospitals and clinics, or even in emergency situations in the field, e.g., in an ambulance or the like. In this technique, the skin, flesh or fascia is simply stapled together, typically using biodegradable staples which do not have to be subsequently removed. Prior art surgical staplers are of various configurations, such as the acute angled "ETHICON-PROMIXATE Model 55 W" in which the two arms of the device are squeezed together to release and implant the staple at the head or apex of the device, or the "AUTO-SUTURE" Disposable Skin Stapler, which is shaped similar to a gun, with the staples being discharged from the outer end of the barrel of the device.

There is an abundance of prior art relative to surgical staplers and the like. Among this body of art may be mentioned the following pertinent U.S. Pat. Nos. 3,472,231; 3,777 355; 3,827,277; 3,844,289; 3,949,923; 4,076,162; 4,101,063; 4,111,206; 4,152,920; 4,244,370; 4,263,903; 4,290,542; 4,316,468 and 4,319,576.

SUMMARY OF THE INVENTION

Purposes of the Invention

It is an object of the present invention to provide an improved surgical stapler for implanting sutures or staples in the skin, flesh or fascia of a human or animal subject, either to close an incision or to repair an internal organ during or after an operation, or to repair a wound or the like.

Another object is to provide an improved disposable surgical stapler.

A further object is to provide a surgical stapler which is easily manipulated due to an improved hypodermic shape and swivel top.

An additional object is to provide a surgical stapler with a geared plunger mechanism which gives a mechanical advantage.

Still another object is to provide a hypodermic configuration for a surgical stapler, so that the surgeon is permitted to suture or staple an incision, wound or internal organ without twisting his hand or the flesh, skin or fascia of the patient.

Still a further object is to provide a surgical stapler with a magazine feed which supplies the sutures or staples to the applying head at an advantageous angle.

Still an additional object is to provide a surgical stapler with gearing (large and small gears) and parallel toothed racks which gives a mechanical advantage.

Yet another object is to provide a surgical stapler with an upstop for the pusher and plunger, which serves to position the top of the pusher, so that in transit the staple cannot get twisted or suck back.

Yet a further object is to provide a surgical stapler with improved visibility when implanting the staples, and in which the staples are visible when coming out of the device, due to the vertical arrangement.

Yet a still further object is to provide a surgical stapler with an advantageous feed angle of the staples, combined with other mechanism in the device, to give improved feeding of the staples via the magazine feed.

Yet an additional object is to provide an improved surgical stapler for implanting sutures or staples in the fascia, skin or flesh of a human subject, so as to close an incision or wound, or to repair internal organs after an operation on a human or animal subject.

These and other objects and advantages of the present invention will become evident from the description which follows.

Brief Description of the Invention

The present invention is characterized by the provision of a surgical stapler for implanting sutures which includes a hollow elongated oblong body, together with means at one end of said body to grasp the body with and between two fingers of a human hand; a generally rectilinear moveable plunger, the plunger extending within and generally parallel to the longitudinal axis of the body; a knob means, the knob means being mounted to the outer end of the plunger, so that the plunger may be manually depressed into the body by a human finger, by pressing on the knob means while manually restraining the aforementioned grasping means; a spring, the spring being mounted within the body and opposed to the inwards movement of the plunger into the body; a rotatable unitary cluster gearing element, the gearing element being mounted within the body, the axis of the gearing element being substantially transverse to the longitudinal axis of the body; the gearing element including a first circular gear and a second circular gear, the gears being joined to each other and coaxially aligned and juxtaposed along the axis of the gearing element, the first gear being of larger diameter than the second gear, with the teeth of the first gear meshing with teeth spaced in a generally rectilinear array along a first toothed rack, the first rack consisting of a portion of the plunger; a generally rectilinear staple pusher element, the pusher element being disposed within the body and depending from a second toothed rack, the teeth of the second rack being spaced in a generally rectilinear array along the second rack and meshing with the second gear, the pusher element terminating with a bifurcated outer end terminus at the head of the stapler body; an anvil, the anvil being mounted to the body and being juxtaposed with the bifurcated terminus of the pusher element, so that staples fed seriatim to the anvil are manipulated into a closed loop configuration by the bifurcated terminus; and a magazine means, the magazine means being mounted integrally with the body adjacent the anvil and containing a plurality of staples, so that staples are fed seriatim to the anvil.

In a preferred embodiment, the magazine means is substantially rectilinear and extends away from the anvil at an acute angle to the body. Typically, the grasping means is swivelably mounted to the body, so that the grasping means may be rotated about the longitudinal axis of the body. Preferably, the plunger includes an integral lateral stop member, the stop member extending inwards from the body and cooperating with a recess or step in the plunger, so that the path of travel of the plunger is restricted in a direction away from the anvil. In overall structure, the present surgical stapler is of a generally hypodermic shape and configuration. Typically, the spring is rectilinear and depends from the plunger, so that the spring and the plunger are generally coaxial and in tandem. In a preferred embodiment, the second gear includes two discrete second sub-gears of substantially the same dimension, the second sub-gears straddling the first gear with one sub-gear on one side of the first gear and the other sub-gear on the other side of the first gear, each of the sub-gears cooperating with a toothed rack associated with the pusher element. Generally, the diameter dimension of the first gear is from about twice to about three times as large as the diameter dimension of the second gear. In most instances, in practice, the sutures or staples are biodegradable.

In summary, the present surgical stapler for implanting sutures basically entails the provisions of a disposable surgical stapler having an overall hypodermic shape and a geared plunger mechanism, which gives a mechanical advantage. One of the improvements is the hypodermic configuration, which permits the surgeon to suture or staple without twisting his hand or the flesh of the patient. A magazine feed supplies the sutures or staples to the applying head at an advantageous angle. The major salient points of distinction of the present configuration are the geared plunger entailing the gearing (large and small gear), and parallel toothed racks, which gives a mechanical advantage; the upstop for the pusher and plunger, which serves to position the top of the pusher, so that in transit the staple cannot get twisted or suck back; the swivel top and hypodermic-like shape and arrangement, which permits the surgeon to suture or staple without twisting his hand, or the flesh or skin of the patient; improved visibility when implanting the staples, the staples are visible when coming out of the device, due to the vertical arrangement; and the advantageous feed angle of the staples, combined with other mechanism in the device, to give improved feeding of the staples via the magazine feed.

The invention accordingly consists of the features of construction, combination of elements and arrangement of parts which will be exemplified in the device and article of manufacture hereinafter described, and of which the scope of application is as elucidated supra and as will be indicated in the appended claims.

BRIEF DESCRIPTION OF THE DRAWINGS

In the accompanying drawings in which is shown one of the various possible embodiments of the invention:

FIG. 1 is a side elevation view of the present surgical stapler;

FIG. 2 is a sectional front elevation view of the stapler;

DETAILED DESCRIPTION OF THE PREFERRED EMBODIMENTS

Figure 3:
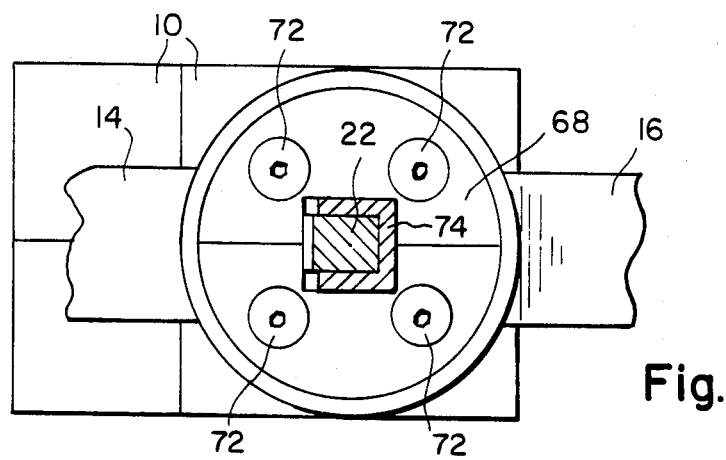
FIG. 3 is a sectional plan view taken substantially along lines 3—3 of FIG. 2.
Figure 4:
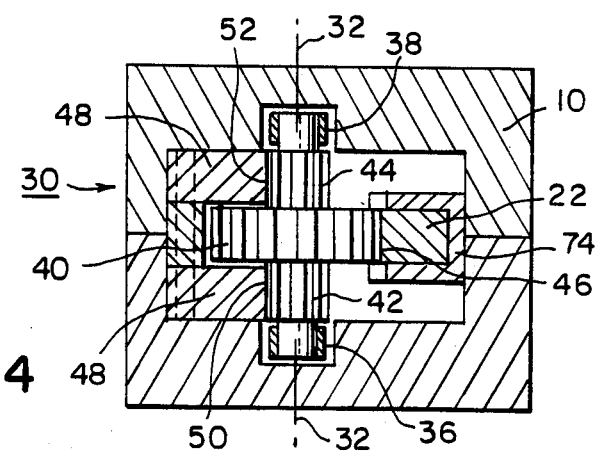
FIG. 4 is a sectional plan view taken substantially along line 4—4 of FIG. 2.
Figure 5:
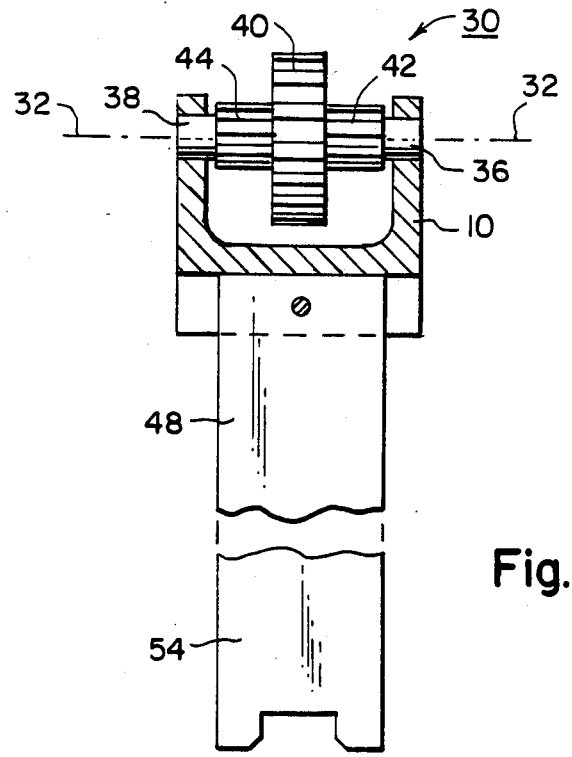
FIG. 5 is a partial sectional elevation view taken substantially along the line 5—5 of FIG. 2

Referring now to the Figures, the overall hypodermic shape and configuration of the present surgical stapler is evident. The stapler is characterized by the provision of a hollow, elongated, oblong body 10, together with means generally designated as 12 at the upper end of the body 10, to grasp the body 10 with and between two fingers of a human hand. Each of the fingers is inserted below a curved portion 14, 16 of a respective arm 18 or 20.

A generally rectilinear movable plunger 22 extends within and generally parallel to the longitudinal axis 23 of the body 10. A knob means, consisting in this case of a knob 24, is mounted to the outer end of the plunger 22, so that the plunger 22 may be manually depressed into the body 10, e.g. by a human thumb, by pressing on the knob 24 while concomitantly manually restraining the grasping means 18, 20, e.g. by the surgeon inserting the forefinger and middle finger of his hand into the respective curved portion 14, 16 of each grasping arm 18, 20. As shown, the grasping means consisting of arms 18 and 20 is swivelably mounted to the body 10, so that the grasping means 18, 20 may be rotated about the longitudinal axis 23 of the body 10.

A spring 26 is mounted within the body 10 and opposed to the inwards (downwards) movement of the plunger 22 into the body 10. As shown, the spring 26 is generally rectilinear and depends from the lower end 28 of the plunger 22, so that the spring 26 and the plunger 22 are generally coaxial and in tandem.

A rotatable, unitary, cluster gearing element, generally designated as 30, is mounted within the body 10. The axis 32 of the gearing element 30 is substantially transverse to the longitudinal axis 23 of the body 10, e.g. as shown, the axis 32 is horizontal while the axis 23 is vertical.

As will appear infra, the mechanical advantage derived from the provision of the cluster gearing element 30 is typically on the order of about 4:1, so that a force 34 exerted via knob 24 onto plunger 22 is multiplied by four times in the appurtenances of the device by means of which the staple or suture is implanted.

In this preferred embodiment of the invention, the cluster gearing element 30 is mounted along axis 32 via trunnions 36, 38, and the gearing element 30 basically consists of a first circular gear 40 and a second circular gear consisting in this case of two discrete sub-gears 42, 44 of generally the same dimension. The second sub-gears 42, 44 straddle the first gear 40, with one sub-gear 42 on one side of the first gear 40, and the other subgear 44 on the other side of the first gear 40. As will appear infra, each of the sub-gears 42, 44 cooperates with a toothed rack associated with a pusher element. As can be seen from the Figures, typically the diameter dimension of the first gear 40 is from about twice to about three times as large as the diameter dimension of the second gear (sub-gears 42, 44). Thus in general, the gears 40 and 42, 44 are joined to each other and coaxially aligned and juxtaposed along the axis 32 of the gearing element 30, and the first gear 40 is of larger diameter than the second gear 42, 44 to give a mechanical advantage as mentioned supra. The teeth of the first gear 40 mesh with teeth spaced in a generally rectilinear array along a first toothed rack 46, the rack 46 consisting of a portion of the plunger 22, as shown.

A generally rectilinear staple pusher element 48 is disposed within the body 10 and depends from a second toothed rack 50, 52, the teeth of the second rack 50, 52 being spaced in a generally rectilinear array along the second rack 50, 52 and meshing with the second gear 42, 44. The pusher element 48 terminates with a bifurcated outer end terminus 54 at the head 56 of the stapler body 10.

An anvil 58 is mounted to the body 10 and juxtaposed with the bifurcated terminus 54 of the pusher element 48, so that staples 60 (typically biodegradable) fed seriatim to the anvil 58 are manipulated into a closed loop configuration by the bifurcated terminus 54.

The surgical stapler is completed by the provision of a magazine means 62 mounted integrally with the body 10 adjacent the anvil 58 and containing the plurality of staples 60, whereby the staples 60 are fed seriatim to the anvil 58. Typically as shown, the magazine means 62 is generally rectilinear and extends away from the anvil 58 at an acute angle 64 to the body 10, the angle 64 typically being about 45 degrees.

In this preferred embodiment of the present invention, an integral lateral stop member 66, consisting in this case of a set screw, is provided. The stop member screw 66 is mounted to a cap plate portion 68 of the body 10, and extends inwards from the body 10 towards the axis 23, and cooperates with a recess or step 70 in the plunger 22, so that the path of travel of the plunger 22 is restricted in a direction away from the anvil 58, i.e. opposite to arrow 34 and upwards. Screws 72 attach the cap plate 68 to the body 10 (FIG. 3). The generally rectangular, e.g. square, plunger 22 rides in a generally U-shaped guide channel or member 74. The spring 26 is typically a cylindrical coil spring, although other spring configurations known to those skilled in the art may be employed in practice.

It thus will be seen that there is provided a surgical stapler for implanting sutures, staples and the like in a human or animal subject which achieves the various objects of the invention, and which is well adapted to meet the conditions of practical use.

As various possible embodiments might be made of the above invention, and as various changes might be made in the embodiments above set forth, it is to be understood that all matter herein described or shown in the accompanying drawings is to be interpreted as illustrative and not in a limiting sense. Thus, it will be understood by those skilled in the art that although preferred and alternative embodiments have been shown and described in accordance with the Patent Statutes, the invention is not limited thereto or thereby, since the embodiments of the invention particularly disclosed and described herein above are presented merely as an example of the invention. Other embodiments, forms, and modifications of the invention, coming within the proper scope and spirit of the appended claims, will of course readily suggest themselves to those skilled in the art. Thus, while there has been described what is at present considered to be the preferred embodiments of the invention, it will be obvious to those skilled in the art that various changes and modifications may be made therein, without departing from the invention, and it is, therefore, aimed in the appended claims to cover all such changes and modifications as fall within the true spirit and scope of the invention.

What is claimed is:

1. A surgical stapler for implanting sutures which comprises:
    (a) a hollow elongated oblong body, together with means at one end of said body to grasp said body with and between two fingers of a human hand,
    (b) a generally rectilinear moveable plunger, said plunger extending within and generally parallel to the longitudinal axis of said body,
    (c) a knob means, said knob means being mounted to the outer end of said plunger, so that said plunger may be manually depressed into said body by a human finger, by pressing on said knob means while manually restraining the grasping means of (a),
    (d) a spring, said spring being mounted within said body and opposed to the inwards movement of said plunger into said body,
    (e) a rotatable unitary cluster gearing element, said gearing element being mounted within said body, the axis of said gearing element being substantially transverse to the longitudinal axis of said body; said gearing element comprising a first circular gear and a second circular gear, said gears being joined to each other and coaxially aligned and juxtaposed along the axis of said gearing element, said first gear being of larger diameter than said second gear, with the teeth of said first gear meshing with teeth spaced in a generally rectilinear array along a first toothed rack, said first rack comprising a portion of said plunger,
    (f) a generally rectilinear staple pusher element, said pusher element being disposed within said body and depending from a second toothed rack, the teeth of said second rack being spaced in a generally rectilinear array along said second rack and meshing with said second gear, said pusher element terminating with a bifurcated outer end terminus at the head of the stapler body,
    (g) an anvil, said anvil being mounted to said body and being juxtaposed with said bifurcated terminus of said pusher element, so that staples fed seriatim to said anvil are manipulated into a closed loop configuration by said bifurcated terminus, and
    (h) a magazine means, said magazine means being mounted integrally with said body adjacent said anvil and containing a plurality of staples, so that staples are fed seriatim to said anvil.

2. The surgical stapler of claim 1 in which said magazine means is substantially rectilinear and extends away from the anvil at an acute angle to the body.

3. The surgical stapler of claim 1 in which the grasping means of (a) is swivelably mounted to the body, so that said grasping means may be rotated about the longitudinal axis of the body.

4. The surgical stapler of claim 1 in which said plunger includes an integral lateral stop member, said stop member extending inwards from said body and cooperating with a recess or step in the plunger, so that the path of travel of the plunger is restricted in a direction away from the anvil.

5. The surgical stapler of claim 1 in which the surgical stapler is of a generally hypodermic shape and configuration.

6. The surgical stapler of claim 1 in which the spring is rectilinear and depends from the plunger, so that the spring and the plunger are generally coaxial and in tandem.

7. The surgical stapler of claim 1 in which the second gear comprises two discrete second sub-gears of substantially the same dimension, said second sub-gears straddling said first gear with one sub-gear on one side of said first gear and the other sub-gear on the other side of said first gear, each of said sub-gears cooperating with a toothed rack associated with the pusher element.

8. The surgical stapler of claim 1 in which the diameter dimension of the first gear is from about twice to about three times as large as the diameter dimension of the second gear.

9. The surgical stapler of claim 1 in which the staples are biodegradable.

10. The surgical stapler of claim 1 in which the mechanical advantage derived from the gearing element is about 4:1.

* * * * *